United States Patent
Henderson

(10) Patent No.: US 9,357,837 B2
(45) Date of Patent: Jun. 7, 2016

(54) OMNIDIRECTIONAL ORAL CARE BRUSH

(71) Applicant: Alan Henderson, Indianapolis, IN (US)

(72) Inventor: Alan Henderson, Indianapolis, IN (US)

(73) Assignee: Carlon Holdings LLC, Indianapolis, IN (US)

( * ) Notice: Subject to any disclaimer, the term of this patent is extended or adjusted under 35 U.S.C. 154(b) by 0 days.

(21) Appl. No.: 14/135,986

(22) Filed: Dec. 20, 2013

(65) Prior Publication Data

US 2014/0173839 A1 Jun. 26, 2014

Related U.S. Application Data

(60) Provisional application No. 61/745,199, filed on Dec. 21, 2012.

(51) Int. Cl.
| | | |
|---|---|---|
| *A46D 3/00* | (2006.01) | |
| *A46B 5/02* | (2006.01) | |
| *A46B 9/04* | (2006.01) | |
| *A61C 17/34* | (2006.01) | |
| *A46B 15/00* | (2006.01) | |

(52) U.S. Cl.
CPC . *A46D 3/00* (2013.01); *A46B 5/023* (2013.01); *A46B 9/045* (2013.01); *A61C 17/3418* (2013.01); *A61C 17/3481* (2013.01); *A46B 15/0097* (2013.01)

(58) Field of Classification Search
CPC .. A46B 5/0054; A46B 5/0058; A46B 5/0066; A46B 15/0097; A46B 9/045; B25G 1/02; B25G 1/10
USPC ............ 15/159.1, 160, 167.1, 167.2
See application file for complete search history.

(56) References Cited

U.S. PATENT DOCUMENTS

| | | | |
|---|---|---|---|
| 1,793,307 A | * | 2/1931 | Dolan .............................. 15/188 |
| 4,828,420 A | | 5/1989 | Otsuka |
| 5,544,383 A | | 8/1996 | Gamble |
| 5,778,478 A | | 7/1998 | Coleman |
| 5,944,519 A | * | 8/1999 | Griffiths .......................... 433/80 |
| 5,956,796 A | * | 9/1999 | Lodato .......................... 15/167.1 |
| 6,076,223 A | * | 6/2000 | Dair et al. .................... 15/167.1 |

(Continued)

FOREIGN PATENT DOCUMENTS

| | | |
|---|---|---|
| CN | 201025977 Y | 2/2008 |
| DE | 202007014401 U1 | 2/2008 |

(Continued)

OTHER PUBLICATIONS

Authorized Officer E Eskina, International Search Report and Written Opinion for International Application No. PCT/US 2013/075266, mailed Apr. 17, 2014, 8 pages.
Authorized Officer Simin Baharlou, International Preliminary Report on Patentability for International Application No. PCT/US 2013/075266, mailed Jul. 2, 2015, 6 pages.

*Primary Examiner* — Laura C Guidotti
(74) *Attorney, Agent, or Firm* — Fish & Richardson P.C.

(57) ABSTRACT

A toothbrush featuring a graspable elongated handle defining a longitudinal axis, the handle comprising a neck region adjacent an end of the handle and a head disposed at the end of the handle. The head is carrying flexible bristles that extend outward from an outer surface of the head. The outer surface of the head is axisymmetric. The bristles are distributed about the head such that bristles extend in each of several radial directions, including from opposite sides of the head. At least some of the bristles are extending so as to overlay the longitudinal axis in opposite directions.

13 Claims, 4 Drawing Sheets

(56) References Cited

U.S. PATENT DOCUMENTS

| | | |
|---|---|---|
| 6,108,869 A | 8/2000 | Meessmann |
| 6,298,516 B1 | 10/2001 | Beals |
| D455,012 S | 4/2002 | Perez |
| D457,727 S | 5/2002 | Ping |
| 6,902,399 B2 * | 6/2005 | Mannschedel ............... 433/141 |
| 7,036,179 B1 | 5/2006 | Weihrauch |
| D586,126 S | 2/2009 | Carey |
| D624,755 S | 10/2010 | Luis |
| 8,584,301 B2 * | 11/2013 | Maissami ............... 15/167.1 |
| 8,857,004 B1 * | 10/2014 | Luis et al. ............... 15/167.1 |
| 2002/0100134 A1 | 8/2002 | Dunn |
| 2003/0088932 A1 * | 5/2003 | Gardiner ............... 15/167.1 |
| 2004/0200748 A1 * | 10/2004 | Klassen et al. ............... 206/368 |
| 2008/0201886 A1 | 8/2008 | Bielfeldt |
| 2010/0050358 A1 | 3/2010 | Kim |
| 2010/0146724 A1 | 6/2010 | Jo |

FOREIGN PATENT DOCUMENTS

| | | |
|---|---|---|
| RU | 2013968 C1 | 6/1994 |
| WO | WO0126504 A1 | 4/2001 |
| WO | WO2009113681 A1 | 9/2009 |
| WO | WO2009157955 A1 | 12/2009 |
| WO | WO2011141577 A1 | 11/2011 |

* cited by examiner

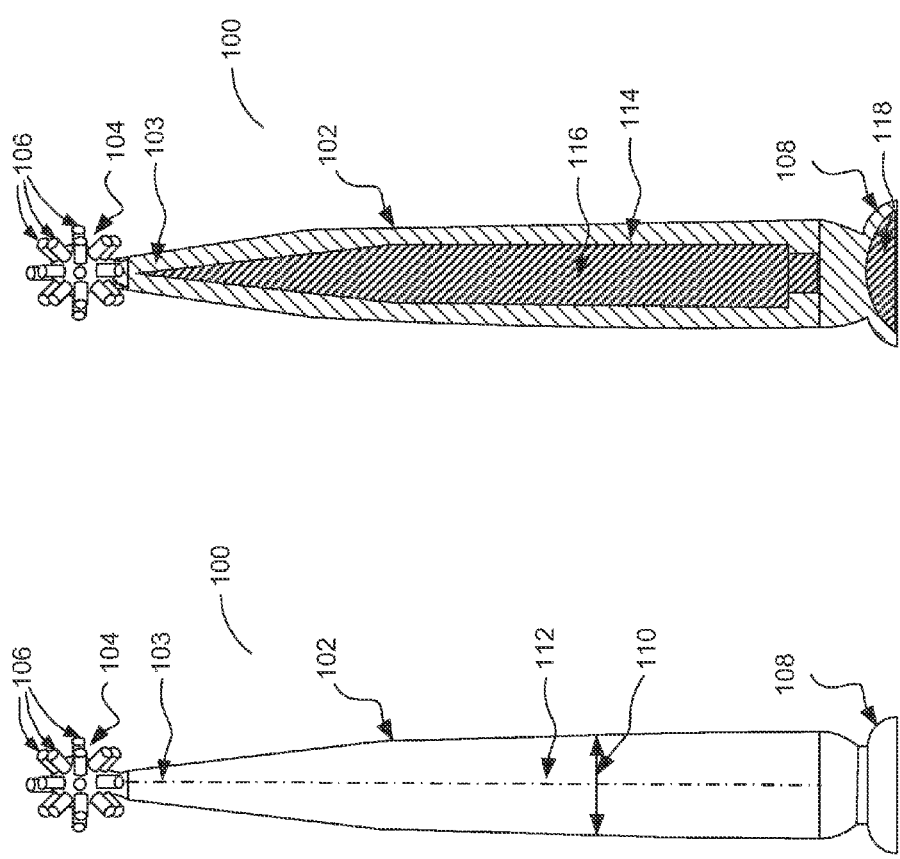

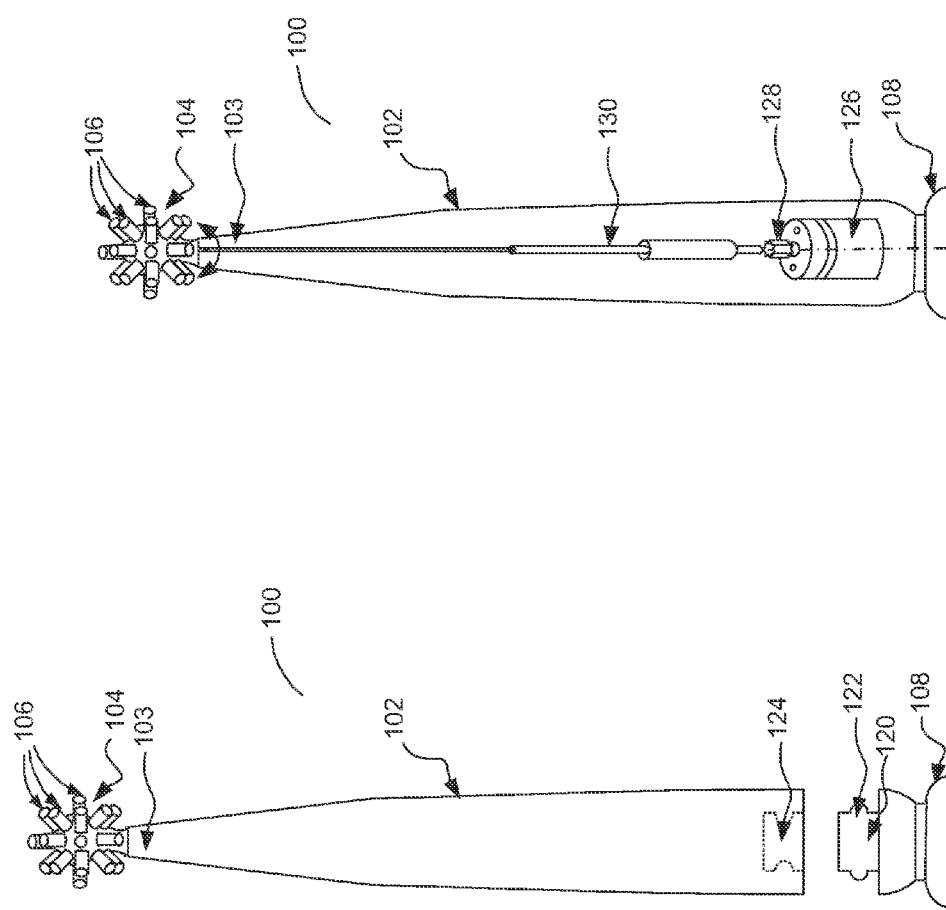

OMNIDIRECTIONAL ORAL CARE BRUSH

CROSS REFERENCE TO RELATED APPLICATIONS

This application claims priority under 35 U.S.C. §119 to U.S. Provisional Patent Application No. 61/745,199, filed Dec. 21, 2012, and entitled "Omnidirectional Oral Care Brush," the entire contents of which are incorporated by reference herein.

TECHNICAL FIELD

The present invention relates to oral care brushes.

BACKGROUND

Toothbrushes are generally designed as oral care brushes useful for cleaning and/or massaging the teeth and/or gums. Cleaning the teeth and/or gums of humans with traditional toothbrushes can raise several problems. The hard backside of traditional toothbrushes can bang against the user's gums and teeth opposite to the region targeted for brushing. The hard handle of the toothbrush can also be abrasive upon contact with the lips and teeth.

In the case of children and people with reduced manual dexterity, the problems associated with toothbrush design can become more acute. For example, infants and children are often not co-operative when parents attempt to brush their teeth, which results into a reduction of the teeth cleaning duration and effectiveness. The use of a traditional infant and children toothbrushes, which target a small dental region at a time for a short time can therefore become an ineffective process.

In many cases, the infants and children attempt to become more independent and wish to brush the teeth themselves. The manual dexterity of infants and children is insufficiently developed and it does not easily allow them to grasp and properly use small thin cylindrical objects (such as a pencil or crayon), as required for an adequate brushing of the teeth and gums.

In some cases, seniors or other people, who suffer from tremors or other conditions affecting manual dexterity, can have difficulties with properly brushing teeth and gums using traditional toothbrushes.

SUMMARY

Various aspects of the invention feature a toothbrush including a graspable elongated handle defining a longitudinal axis the handle with a neck region adjacent to an end of the handle and a head disposed at the end of the handle and carrying flexible bristles that extend outward from an outer surface of the head. The outer surface of the head is axisymmetric and the bristles are distributed about the head such that bristles extend in each of several radial directions, including from opposite sides of the head at least some of the bristles extending so as to overlay the longitudinal axis in opposite directions.

In some implementations, the outer surface of the handle in the neck region has a lower hardness than the outer surface of the head. The outer surface of the head, on a side of the head opposite the handle, is hemispherical. The bristles extend perpendicular to the longitudinal axis.

According to one aspect of the invention, the outer surface of the head is axisymmetric with respect to the longitudinal axis of the handle. The outer surface of the head is generally oval in shape. The bristles below a widest part of the head extend perpendicular to the longitudinal axis.

In some implementations, the toothbrush includes a suction cup pedestal at an end of the handle opposite the head. In some implementations, the head has a maximum diameter of 15 mm and each of the plurality of bristles has a maximum length of 0.5 mm. In some implementations, the handle is bulbous. The handle is of a circular cross-section. For example, the handle has an outer diameter that has a local minimum in the neck region In some implementations, the handle comprises a soft overlay constructed such that the soft overlay is not abrasive at contact with lips and teeth.

In some examples, the toothbrush includes a motor located in the handle the motor activating an oscillation or spinning of the round head Another aspect of the invention features a method of making a toothbrush. The method includes forming a lower toothbrush head section by anchoring lower bristle tufts in a lower toothbrush head shell having a circular rim, with the lower bristle tufts extending in multiple radial directions, forming an upper toothbrush head section by anchoring upper bristle tufts in an upper toothbrush head shell having a circular rim, with the upper bristle tufts extending in multiple radial directions and then spin-welding the rims of the upper and lower toothbrush head section shells together to form a sealed toothbrush head.

In some examples, the lower toothbrush head section, as formed, includes a graspable handle extending from a side of the lower toothbrush head shell opposite the circular rim of the lower toothbrush head shell. The upper toothbrush head shell defines an interior cavity. In some examples, anchoring the upper bristle tufts in the upper toothbrush head shell includes securing the upper bristle tufts in holes extending into the interior cavity, and then sealing the holes prior to spin-welding the rims of the upper and lower toothbrush head section shells together.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a side view of a toothbrush with a round head.

FIG. 1B is a partial sectional view of the toothbrush of FIG. 1A, showing construction of the handle.

FIG. 1C shows a version of the toothbrush of FIG. 1A, with a detachable section cup pedestal base.

FIG. 1D is a schematic representation of a version of the toothbrush of FIG. 1A, with a motorized head.

DETAILED DESCRIPTION

Figure 2A:
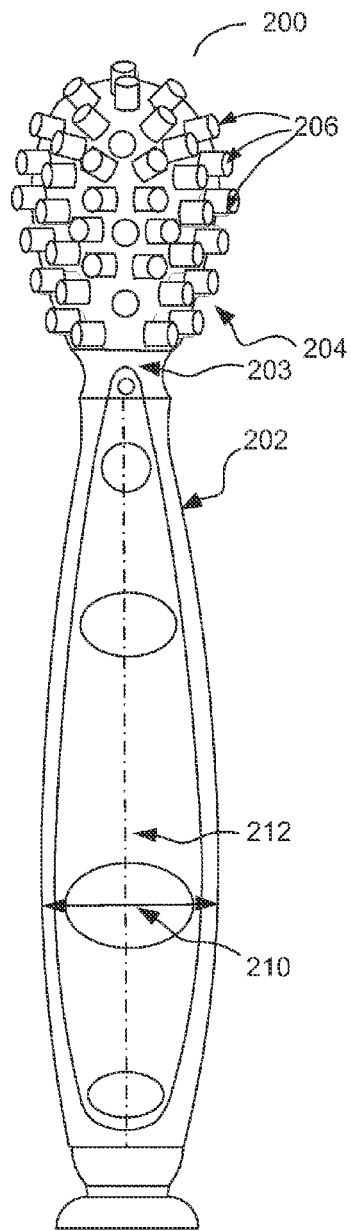
FIG. 2A is a side view of a toothbrush with an oval head.

Referring first to FIG. 1A, toothbrush 100 has a round head. The toothbrush includes a handle 102, a head 104 carrying multiple bristles 106, and a suction cup pedestal 108.

The handle 102 is bulbous, having a graspable elongated shape and circular cross-section. Handle 102 defines a neck region 103 a longitudinal axis 110 and a main body section 112 extending along the longitudinal axis 110. The neck region 103 of the handle is adjacent to head 104.

Some embodiments of the toothbrush can be designed for infants. To give a perspective on the size of an infant toothbrush, with reference to the example shown in FIG. 1A, the toothbrush 100 has an overall length of about 130 mm, and the diameter of the main body section of handle 102 is about 15 mm. The handle 102 has an outer diameter that has a local minimum in the neck region 103. As discussed below, the outer surface of the handle 102 in the neck region 103 has a lower hardness than the outer surface of the head 104.

In some implementations, as illustrated in FIG. 1B, the handle 102 is formed of two concentric parts, a hard core 116 and a soft outer layer 114. In some implementations, the hard core 116 extends from the base of the handle 102 to the neck region 103 of the handle 102. In some implementations, the hard core 116 extends only through a part of the handle 102. The soft outer layer 114 is overmolded onto hard core 116 to provide a soft bite surface in the neck region 103 and also a grip surface on the main body section of the handle. In other examples, hard core 116 extends into head 104 and in some cases also forms the outer surface of the head. In some cases, the suction cup pedestal 108 also includes a hard core 118, which can be formed as an extension of the hard core 116 within the handle 102. In some implementations, the hard core 118 of the suction cup pedestal 108 is completely separated from the hard core 116 within the handle 102. The soft outer layer 114 is a flexible elastomeric material that is resistant to degradation as a result of mechanical stress (e.g. infant chewing), heat, cold, exposure to sunlight and exposure to moist conditions. The soft outer layer 114 is preferably very fatigue resistant, and may be formed of a thermoplastic elastomer. The soft outer layer 114 is preferably paraben- and phthalate-free. The soft outer layer 114 may have a varying thickness, such as a thickness of approximately 2-3 mm in handle grip regions, and thinner in the neck region.

The head 104 is disposed at the end of the handle 102, adjacent the neck region 103. In this example, the surface of head 104 from which the bristles 106 extend is generally of round shape. In some implementations, head 104 can have a theme design particular for infants, children, or adults in general. For example, the head 104 can be designed to resemble a sports ball (e.g. basketball, baseball, tennis, soccer). The lateral extent of the head 104, perpendicular to the longitudinal axis 110, is greater than the lateral extent of the handle 102 in the neck region 103. The lateral extent of the head 104 is sized to be inserted between upper and lower gums of a human infant, and preferably is of a diameter no more than about 15 mm. In this example, the outer surface of head 104 from which bristles 106 extend has a diameter of about 5 mm Head 104 carries multiple flexible bristles 106 that extend outward from an outer surface of the head 104. The bristles 106 are distributed around the head 104 to extend in several directions. In some implementations, the bristles form a substantially spherical shape, the bristles projecting from the head surface in essentially all directions not occupied by the neck of the toothbrush. They may include bristles extending substantially parallel to the longitudinal axis 110 of the toothbrush from the top of the head. In some cases, different tufts of bristles extend perpendicular to the longitudinal axis 110 in different radial directions from the side of the head, enabling simultaneously brushing of both the upper and the lower teeth, and avoiding the need to rotationally orient the toothbrush for use. Some bristles extend in acute or obtuse angles, meaning that projections of the bristles overlie the longitudinal axis of the toothbrush. Preferably, tufts below a longitudinal center of the head are angled to extend relatively downward, while those above the longitudinal center (or equator, in the case of a spherical head) extend relatively upward. In some cases the tufts all extend along radial lines emanating from a common head center. In some implementation, the bristles are uniformly distributed over the surface of the head 104. In some implementation, the bristles are more densely distributed in the equatorial region, which includes the bristles that are most frequently used. As shown in the figures, bristles 106 are distributed around the head 104 to extend from opposite sides of the head 104, such that the bristles overlay the longitudinal axis 110 in opposite directions. The bristles 106 can be made from synthetic (e.g. nylon and polyester) or natural material (e.g. boar's hair). In some implementations, all bristles 106 have the same length. For an infant toothbrush, each of the bristles 106 has a maximum length of 0.5 mm.

Bristles 106 may be drawn polymer filaments firmly secured to the head body to prevent pull-out during use. Such filaments may be secured as tufts within holes molded into the head surface, for example, as is known in the art of toothbrush manufacture. In another example, bristles 106 are in the form of molded protrusions of elastomeric material forming the outer surface of head 104. Such protrusions should be longer than their width, and of sufficient bending flexibility to deflect under light pressure from an infant's gums, but sufficiently strong to avoid tearing from biting. Alternatively, such projections may be formed of a digestible material, or a material that is otherwise safe for ingestion in small pieces.

The suction cup pedestal 108 is concentrically connected to the lower end of the handle 102, opposite head 104. The suction cup pedestal 108 includes a cup of compliant (e.g., elastomeric) material with a smooth rim, such that light pressure of the rim against a smooth, nonporous horizontal surface partially collapses the cup and retains the pedestal against the surface, thereby keeping toothbrush 100 vertical and head 104 spaced from the surface in order to help prevent contamination.

As illustrated in FIG. 1C, suction cup pedestal 108 is retained on handle 102 by a snap fit 122. A projection 120 of suction cup pedestal 108 is received in an aperture 124 in the end of the handle, with a circumferential recess within the aperture 124.

As illustrated in FIG. 1D, the toothbrush 100 can include a motor 126. The motor may be coupled to the head by an appropriate transmission in order to cause the head to spin, vibrate or to move with respect to the handle. Vibration may be induced by motor rotor imbalance, and the motor can be set to rotate at a speed that induces a desired gum massaging frequency. In another example, the motor 126 makes the entire head oscillate back and forth. In another example, the motor 126 makes the entire head spin relative to the longitudinal axis 110.

In the illustrated example, shown schematically, motor 126 is sealed within the lower end of the handle 102, and coupled to the head 104 via a drive shaft 130 and coupling 128. The handle 102 includes an on/off switch (not shown) for controlling the motor 126, and may include batteries and/or a power receptacle, for powering the motor. The handle 102 includes a dial (not shown) for controlling the speed of oscillation or spinning generated by the motor 126. The handle 102 includes a dial (not shown) for controlling the level of frequency generated by the motor 126. The handle 102 may also include a battery (not shown), for driving the electrical motor. The battery can be a rechargeable type of battery or a single use type of battery. The suction cup pedestal 108 can include an electrical assembly to charge the battery while the handle 102 is attached to the suction cup pedestal 108. The suction cup pedestal 108 includes an electrical cord for connecting the motor 126 or the rechargeable battery to an electrical source.

FIGS. 2A-D illustrate a second example of an oral care brush 200, similar in use to the first example of an oral care brush 100. Oral care brush 200 has an oval head 204. Head 204 can have a design particular for girls, for boys, or adults, in general. For example, the head 204 can be designed to resemble a sports ball (e.g. a football). In some embodiments, all bristles 206 below the widest part of the head 204 project sideways, and not at an angle with respect to the axis. The handle 202 has an axisymmetric shape with a variable outer diameter 210. The outer diameter 210 has a maximum in the lower half of the handle and a local minimum in the neck region 203.

In some embodiments, the size of the brush will depend on the target age group. For example, an infant toothbrush 200 can have an overall length of about 190 mm, and a diameter of the main body section of handle 202 of about 23 mm. The lateral extent of the head 204 is preferably of a diameter no more than about 25 mm. The outer surface of head 204 from which bristles 206 extend has a diameter of about 9 mm. For an infant toothbrush, the head has a maximum diameter of the cross-section perpendicular on the longitudinal axis 212 of 19 mm and an approximate length of 25 mm.

Figure 2B:
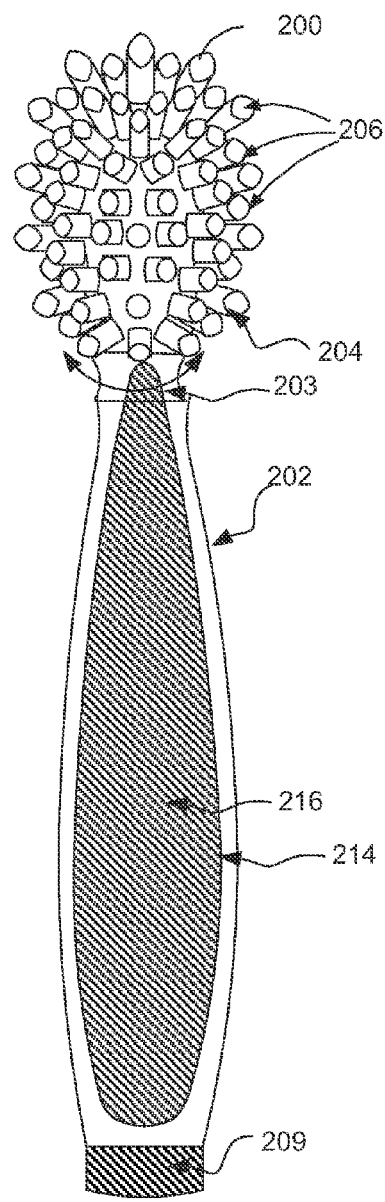
FIG. 2B is a front view of the toothbrush of FIG. 2A.
Figure 2C:
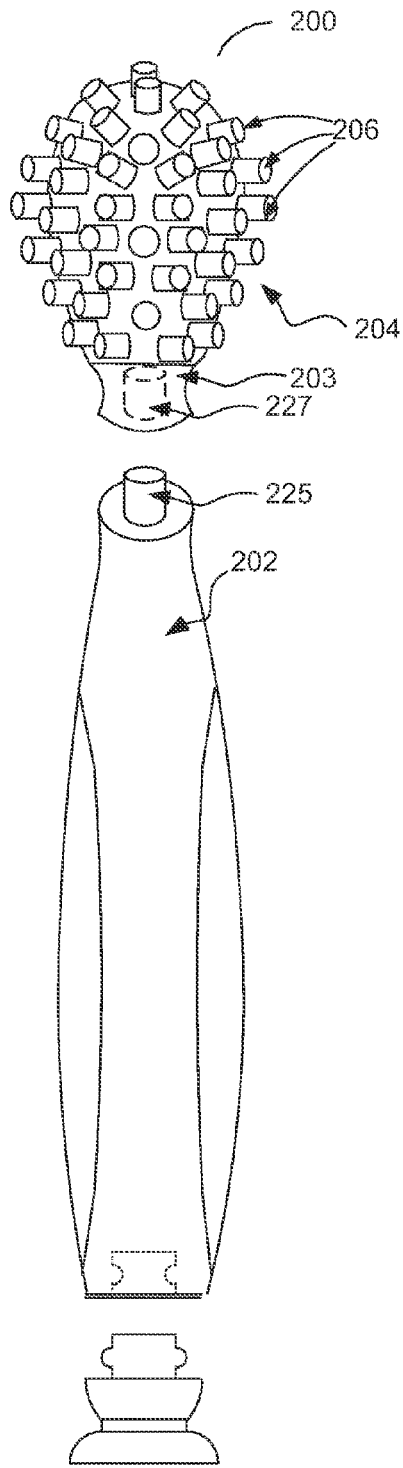
FIG. 2C is a detailed view of the toothbrush of FIG. 2A, showing attachment of the head and base.

In some embodiments, as illustrated in FIG. 2B, the bristles 206 attached to the head 204 are arranged in alternating sections of bristle length from longer to shorter to longer creating a wavy looking head 204. In some implementations, each of the plurality of bristles 206 has a maximum length of 0.5 mm. In some embodiments, a weighted base 209 is attached to the lower end of the handle 202. The weighted base 209 supports the toothbrush 200 in the vertical position. In some embodiments, the handle 202 is formed of two concentric parts, a hard core 216 and a soft outer layer 214. In some embodiments, the hard core 216 extends from the base of the handle 202 to the neck region 203 of the handle 202. The shape of the hard core 216 is similar to the shape of the handle 202. Referring next to FIG. 2C, the head 204 with the neck region 203 can be detached from the handle 202. Head 204 can be retained on handle 202 by a snap fit. A projection 225 of handle 202 is received in an aperture 227 in the end of the neck region 203, with a circumferential recess within the aperture 227. The projection 225 and the aperture 227 are designed to optimally transmit the motion generated by the motor in the engaged position. The bristles 206 attached to the middle section of the head 204 are longer than the bristles attached to the top and bottom of the head 204.

Figure 2D:
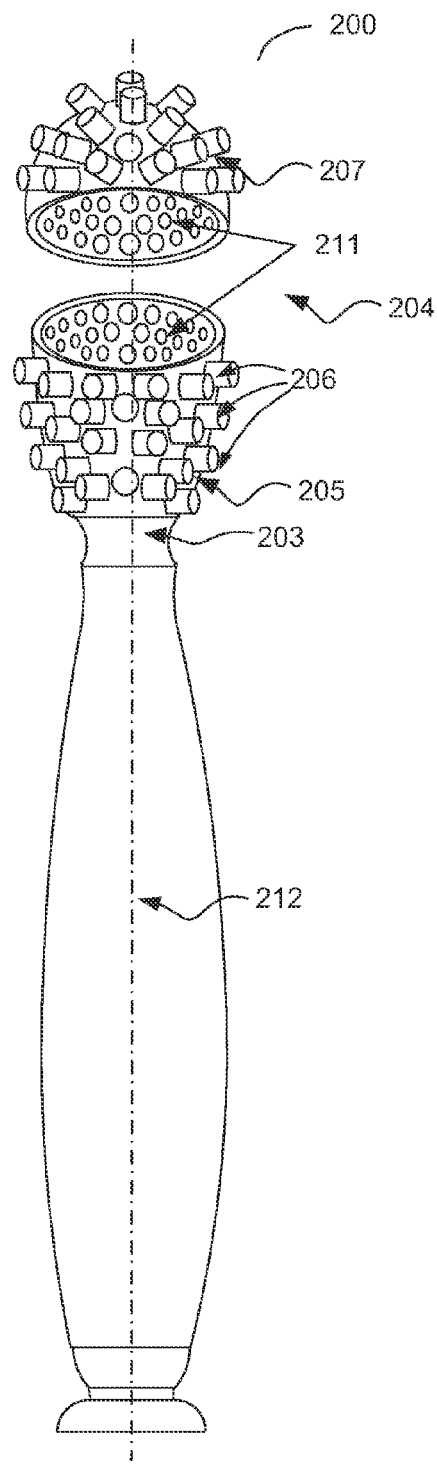
FIG. 2D is a schematic representation of a version of the toothbrush of FIG. 2A, also illustrating a method of making the toothbrush.

As illustrated in FIG. 2D, the head 204 of the toothbrush 200 can be formed from two head shell 205 and 207, the lower head shell 205 being connected to the handle 202. Each of the two head shells 205 and 207 include an inner surface 211, on which the bristles 206 are installed and firmly anchored, to prevent detachment during brushing. Individual bristle tufts may be inserted through open holes and anchored at the inner surface of the head portions, with the inner surface 211 then sealed, such as with a molded overlay or sealant, preventing infiltration of fluids from outside. The lower head shell 205 may be attached to the upper head shell 207 by any suitable method. For example, the lower head shell 205 and the upper head shell 207 may be welded together, such as by spin welding by rotating upper head shell 207 at a high speed, after installation of all bristle tufts, and then engaging the rim against the rim of the lower head shell 205 while the lower head shell 205 is held stationary. Such spin-welding causes the two rims to fuse and form a sealed head cavity, and advantageously does not require adhesives. Other suitable examples for attaching, connecting, etc. the lower head shell 205 and the upper head shell 207 include snap fit, overmolding, interference fit, pins, thermal bonding and solvent bonding.

A number of embodiments of the invention have been described. Nevertheless, it will be understood that various modifications may be made without departing from the spirit and scope of the invention. Accordingly, other embodiments are within the scope of the following claims.

What is claimed is:

1. A toothbrush comprising:
a graspable elongated handle defining a longitudinal axis, the handle comprising a neck region adjacent an end of the handle and being formed of a hard core surrounded by a soft outer layer, the soft outer layer having a varying thickness that is thinner in the neck region than in handle grip regions; and
a head disposed at the end of the handle and carrying flexible bristles that extend outward from an outer surface of the head,
wherein the outer surface of the head is axisymmetric and wherein the bristles are distributed about the head such that bristles extend in each of several radial directions, including from opposite sides of the head, at least some of the bristles extending so as to overlay the longitudinal axis in opposite directions and the soft outer layer of the handle has a lower hardness than the core of the handle and the outer surface of the head.

2. The toothbrush of claim 1, wherein the outer surface of the head, on a side of the head opposite the handle, is hemispherical.

3. The toothbrush of claim 1, wherein some of the bristles extend perpendicular to the longitudinal axis.

4. The toothbrush of claim 1, wherein the outer surface of the head is axisymmetric with respect to the longitudinal axis of the handle.

5. The toothbrush of claim 1, wherein the outer surface of the head is generally oval in shape.

6. The toothbrush of claim 5, wherein the bristles below a widest part of the head extend perpendicular to the longitudinal axis.

7. The toothbrush of claim 1, wherein the outer surface of the head is generally round in shape.

8. The toothbrush of claim 1, further comprising a suction cup pedestal at an end of the handle opposite the head.

9. The toothbrush of claim 1, wherein the head has a maximum diameter of 15 mm and each of the bristles has a maximum length of 0.5 mm.

10. The toothbrush of claim 1, wherein the handle is bulbous.

11. The toothbrush of claim 1, wherein the handle is of a circular cross-section.

12. The toothbrush of claim 11, wherein the handle has an outer diameter that has a local minimum in the neck region.

13. The toothbrush of claim 1, further comprising a motor located in the handle, the motor activating at least one of an oscillation and spinning of the head.

* * * * *